United States Patent [19]

Pergande et al.

[11] Patent Number: 6,124,326

[45] Date of Patent: *Sep. 26, 2000

[54] USE OF FLUPIRTINE FOR THE PROPHYLAXIS AND THERAPY OF DISORDERS WHICH ARE ASSOCIATED WITH AN UNPHYSIOLOGICALLY HIGH CELL DEATH RATE

[75] Inventors: Gabriele Pergande, Offenbach; Werner E. Müller, Wiesbaden, both of Germany; Neville Osborne, Eynshem Oxford, United Kingdom; Heinz Ulrich, Niedernberg, Germany

[73] Assignee: ASTA Medica Aktiengesellschaft, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/873,124

[22] Filed: Jun. 11, 1997

[30] Foreign Application Priority Data

Jun. 27, 1996 [DE] Germany .................. 196 25 582

[51] Int. Cl.[7] .................................................. A61K 31/44
[52] U.S. Cl. .............................................................. 514/352
[58] Field of Search ............................................... 514/352

[56] References Cited

U.S. PATENT DOCUMENTS

| | | | |
|---|---|---|---|
| 4,481,205 | 11/1984 | von Bebenburg et al. | 424/263 |
| 5,336,689 | 8/1994 | Weber et al. | 514/634 |
| 5,462,965 | 10/1995 | Roba et al. | 514/443 |
| 5,721,258 | 2/1998 | Schwarz et al. | 514/352 |

FOREIGN PATENT DOCUMENTS

WO 97/17072  5/1997  WIPO .

OTHER PUBLICATIONS

Medline abstract AN 95220493, Perovic, S. et al., European Journal of Pharmacology, 288(1), pp. 27–33, Dec. 15, 1994.
Zimmer et al., British Journal of Pharmacology 123: 1154–1158, 1998.
Evans, Ophthalmology, New York: Oxford Univ. Press, pp. 55–78, 1995.
Shandra et al., "Experimental Brain Trauma: Effects of Vitamin Treatment", Journal of Neurotrauma, Jun. 1995, vol. 12, No. 3, PB200, p. 489, XP002043183.
Osborne et al., "Protection of Rabbit Retina From Ischemic Injury by Flupirtine", Investigative Ophthalmology & Visual Science, Feb. 1996, vol. 37, No. 2, pp. 274–280, XP002043185.
S. Perovic et al., "Flupirtine Increases the Levels of Glutathione and Bcl–2 in hNT (human Ntera/D1) Neurons: Mode of Action of the Drug–mediated Anti–apoptotic Effect", European Journal of Pharmacology, vol. 317, No. 1, Dec. 1996, pp. 157–164, XP000673257.
Powell–Jackson et al., "Use of *Flupirtine Maleate as an Analgesic in Patients with Liver Disease", The British Journal of Clinical Practice, Feb. 1985, vol. 39, No. 2, pp. 63–66, XP 002043186.

*Primary Examiner*—Allen J. Robinson
*Attorney, Agent, or Firm*—Cushman Darby & Cushman IP Group of Pillsbury Madison & Sutro LLP

[57] ABSTRACT

The invention relates to the use of flupirtine or its salts for the production of a medicament for the prophylaxis and therapy of disorders which accompany an unphysiologically high cell death rate.

Of particular importance here is the treatment of organ disorders with cell-destroying processes, such as myocardial infarct, shock kidney, shock lung, senile macular degeneration or traumas as a result of mechanical, thermal, radiation or toxic influences.

6 Claims, No Drawings

USE OF FLUPIRTINE FOR THE PROPHYLAXIS AND THERAPY OF DISORDERS WHICH ARE ASSOCIATED WITH AN UNPHYSIOLOGICALLY HIGH CELL DEATH RATE

BACKGROUND OF THE INVENTION

1. Field of the Invention

The invention relates to the use of flupirtine or its salts as medicaments for the prophylaxis and therapy of disorders with an unphysiologically high cell death rate.

2. Background Information

Flupirtine is a known centrally active, non-opiate analgesic which has been introduced in Germany and is licensed, inter alia, for the therapy of neuralgia, pain in wear-related joint disorders, headaches and post-operative pain.

Flupirtine displays its analgesic actions by means of other mechanisms of action than the opiate/opioid analgesics (Nickel, B., Postgrad, Med. J. 63 (Suppl.3), 19 (1987); Szelenyi, I., Nickel B., Borbe, H. O., Brune K., Br. J. Pharmacol. 143,89 (1989)). In electrophysiological investigations, it has been shown that flupirtine is able to intervene both on the supraspinal and on the spinal level in the nociceptive process (Carlsson, K. H., Jurna, I., Eur. J. Pharmacol. 143,89 (1987); Bleyer, H., Carlsson, K. H., Erkel, H. J., Jurna, I., Eur. J. Pharmacol. 151,259 (1988); Nickel, B., Aledter, A., Postgrad, Med. J. 63 (Suppl.3) 41 (1987)).

Besides good analgesic properties, flupirtine has muscle-relaxant properties, so flupirtine can also be employed for the treatment of muscle sprains or in disorders which are based on muscle sprains (DE 40 22 442).

In addition, during investigations of the muscle-relaxant action of flupirtine in the rat, it was found that the flupirtine action can be inhibited by the excitatory amino acid N-methyl-D-aspartate (NMDA). On the basis of this NMDA-antagonistic action, flupirtine is also suitable for the treatment of NMDA-mediated CNS disorders, such as, for example, cerebral ischemia, neurodegenerative disorders, [sic] epileptic fits (DE 43 27 516).

Looked at chemically, flupirtine is 2-amino-3-ethoxycarbonylamino-6-(p-fluorobenzylamino)pyridine.

The synthesis of flupirtine and its pharmaceutically utilizable salts is described in the patents DE 17 95 858, DE 31 33 519 and DE 34 16 609.

SUMMARY OF THE INVENTION

Surprisingly, it has now been found that flupirtine is able to increase the expression of Bcl-2 and to inhibit necrotic processes.

The possibility thus opens up of employing flupirtine for the treatment of disorders which accompany an unphysiologically high cell death rate.

In particular, disorders which are associated with local tissue death as the most severe consequence of a local metabolic disorder, for example as a result of hypoxic, mechanical, thermal, toxic or radiation exposure, can thus be treated.

In the body, the death of cells can take place in two different ways: by apoptosis or necrosis.

While apoptosis (programmed cell death, "cell suicide") is an active process-of cell destruction, necrosis is a result of non-specific damage, in particular to the cell membrane.

The pathological characteristics of necrosis differ from those of apoptosis. Apoptosis is characterized by a shrinkage of the cell, condensation of the chromatin and characteristic evaginations of the cell membrane. At the DNA level, fragmentation into fragments of size 180 base pairs takes place due to endonucleases (characteristic ladder pattern in gelelectrophoresis). The cell disintegrates without release of constituents of the cytoplasm, into membrane-enclosed apoptosis bodies. These are quickly recognized as a result of their modified surface structure of specific receptors of localized macrophages and epithelial cells and are completely phagocytized; an inflammatory reaction is typically absent (Amling et al. 1994, Savill, 1994, Kerr et al. 1994).

In contrast to apoptosis, in the case of cell death by necrosis the plasma membrane is destroyed and the contents of the cell are released into the extracellular space. This leads to tissue damage and inflammatory reactions (Savill, 1994, Kerr et al. 1994). The cell destruction is associated with the release of lactate dehydrogenase (LDH). LDH is a cytoplasmic enzyme and a constituent of all tissues. In the case of organ damage, it can cross into the plasma and is increased in many pathological conditions, inter alia after myocardial infarct, and in acute hepatitis or toxic liver damage.

Not only is the nature and the intensity/duration of the process causing cell death crucial, whether it results in apoptotic or necrotic damage; necrotic and apoptotic processes can also occur simultaneously in the tissue (Yoshimura et al. 1996).

It is known from the literature that programmed cell death (apoptosis) can be inhibited by Bcl-2, a 25 kDa membrane protein having 239 amino acids. The protein is localized in the nuclear membrane, parts of the endoplasmic reticulum and the outer and inner mitochondrial membrane. The mechanism of action of Bcl-2 has still not been completely clarified and, inter alia, the following possible mechanisms are discussed: modulation of the mitochondrial function, indirect antioxidative action, direct prevention of chromatin cleavage, regulation of the cytosolic $Ca^{2+}$ concentration, modulation of the transport of proteins through the nuclear membrane, indirect anti-apoptotic action due to inhibition of the apoptosis-inducing protein Bax (Hale et al. 1996, Park et al. 1996).

DETAILED DESCRIPTION OF THE INVENTION

The novel action of flupirtine according to the invention is intended to be illustrated in greater detail with the aid of the pharmacological investigations.

Pharmacological Investigations

Influence of Flupirtine on BCL-2 Expression

Material and methods

Material

The following reagents were ordered: poly-L-lysine ($M_r$>300,000), glycine, (3-[4,5-dimethylthiazol-2-yl]-2,5-diphenyltetrazolium bromide; Thiazolyl Blue [MTT], Dulbecco's Modified Eagle's Medium (DMEM/HG; containing 4.5 g/l of glucose without glutamine) and Minimum Essential Medium—Eagle [without methionine, cysteine and L-glutamine] (MEM) from Sigma (St. Louis, Mo., USA);

L-glutamine from Biochrom (Berlin); [$^{35}$S]methionine/cysteine from ICN Radiochemicals (Irvine, Calif.; USA) and monoclonal antibodies against human Bcl-2 (raised in the mouse) from Santa Cruz Biotechnology (Santa Cruz, Calif., USA).

Flupirtine maleate [2-amino-3-ethoxycarbonylamino-6-(4-fluorobenzylamino)pyridine maleate] ($M_r$: 420.41) (ASTA-Medica AG). hNT neurons, hNT neuron conditioned medium and hNT neuron inhibition medium (Stratagene, Heidelberg).

hNT Neurons hNT neurons were cultured as described (Younkin et al., 1993; Pleasure and Lee, 1993). They were cultured in the first period in hNT neuron inhibition medium and during the three following weeks in hNT neuron-conditioned medium, as described in the use instructions of Stratagene. hNT neurons [4 weeks old] (Younkin et al., 1993) were treated with various concentrations of glutamate in saline solution which contained 120 mM NaCl, 5.4 mM KCl, 1.8 mM $CaCl_2$, 15 mM glucose and 25 mM Hepes [pH 7.4]. In the experiments, the salt solution was additionally supplemented with 50 μM glycine. The cells were incubated at 37° C. for 30 min with glutamate. After incubation, the salt solution was removed and replaced with DMEM/HG which contained 2 mM glutamine, 100 mU/l of insulin, 0.1 U/ml of penicillin and 0.1 U/ml of streptomycin. The incubation was continued for a further 24 hours.

Flupirtine was added to the cells 2 hours before adding glutamate.

Metabolic Labelling and Quantitative Determination of the Immunoprecipitation of Bcl-2 hNT neurons were metabolically labelled in the presence of 100 μCi/ml of [$^{35}$S]methionine/cysteine in MEM [without methionine, cysteine and L-glutamine] supplemented with 1% bovine serum albumin. The cells were harvested and lysed in the presence of 0.4% SDS and trichloroacetic acid.

Antibody-binding material was immunoprecipitated with the monoclonal anti-Bcl-2 antibody as described (Oltvai et al., 1993; Dole et al., 1994). The resulting immunoprecipitate was separated according to the size of its proteins by means of a 12.5% SDS-polyacrylamide gel and further processed as described (Castle et al., 1993).

For the semi-quantitative analysis of the bands on the autoradiogram, the bands were scanned with an integrating densitometer (Shimadzu CS-910/C-R1A).

Immune staining

The cells were fixed with methanol, which contained 0.02% ethylene glycol bis(β-aminoethyl ether) N,N,N,N-tetraacetic acid [EGTA] at −20° C., as described (Bachmann et al., 1986). The cells were then incubated with monoclonal Bcl-2 [raised against human antigen] antibodies; the immune complexes were visualized using FITC-labelled anti-mouse Ig.

Results

Influence of Flupirtine on the Expression of Bcl-2

The expression of Bcl-2 in hNT neurons was determined using two different techniques. Firstly, Bcl-2 was localized using the microfluorescence method. Cells which were either untreated or were pretreated with 10 μM flupirtine for 2 hours were fixed and incubated with antibodies against Bcl-2. The immune complexes were then visualized using a fluorescence microscope. Cells which had been treated with flupirtine show a clearly intensified staining pattern for Bcl-2 compared with the control group. This observation points to the fact that flupirtine induces the Bcl-2 expression.

In order to support this conclusion further, another process, immunoprecipitation of metabolically labelled Bcl-2, was used. hNT neurons were incubated with [$^{35}$S] methionine/cysteine. The resulting immune complexes were precipitated using monoclonal anti-Bcl-2 antibodies and the proteins were separated according to their size. In the autoradiogram, the 26 kDa Bcl-2 protein is visible in extracts of control samples together with the 31 kDa band, which was already observed earlier by Oltvai et al. (1993). If the intensity of the 26 kDa Bcl-2 band is set equal to 100%, cells which were incubated with 1 mM glutamate show a considerably reduced expression of Bcl-2, ~80%. Incubation of hNT neurons with glutamate together with increasing concentrations of flupirtine (3 and 10 μM) led to a >6-fold increase in Bcl-2.

Influence of Flupirtine on Necrosis

Material and methods:

Cortical nerve cell culture:

The forebrain of 16–18-day-old foetal rats was used. The meninges were removed and the dissociated cortical cells ($1.5$–$2.10^6$) were inoculated on 35 mm Petri dishes which were coated with 0.1 mg/ml poly-D-lysine and were then blocked with serum-containing medium (Dulbecco's Modified Eagle's Medium—DMEM, mixed with 4 mM L-glutamine, 100 U/ml penicillin/100 mg/ml streptomycin, 10% foetal calf serum).

The primary cultures were cultured in DMEM which [lacuna] with L-glutamine (4 mM)—glucose (6 g/l), penicillin (100 U/ml), streptomycin (100 mg/ml) and 10% "hormone medium", to which transferrin (1 mg/ml), insulin (250 mg/ml), putrescine ($6.10^{-4}$M), sodium selenite ($3\times10^{-7}$M), progesterone ($2.10^{-7}$M) and oestradiol ($10^{-11}$M) were added. The cultures were kept in this medium under 5% $CO_2$/95% air in a moisture-saturated atmosphere at 37° C. for at least 7 days.

Hypoxia and reoxygenation:

7 days after inoculation, the cortical neurons were incubated for 5 h in an anoxic atmosphere (95% N/5% $CO_2$) at 37° C. in DMEM 1 g/ml; containing. glucose with L-glutamine and penicillin/streptomycin without "hormone medium". For reoxygenation, the cells were exposed to normoxic conditions (95% air /5% $CO_2$) for 3 h. The control cultures were kept under normoxic conditions. Flupirtine was added to the culture before hypoxia.

Lactate dehydrogenase assay:

The cell damage was measured by means of the lactate dehydrogenase (LDH) release in the cell culture supernatant after hypoxia/reoxygenation. The LDH activity was determined by spectroscopy; pyruvate (0.6 mM) was incubated at 25° C. in phosphate buffer pH 7.5 with reduced nicotinamide adenosine dinucleotide (NADH) 0.18 mM in the presence of the sample to be investigated (50 mM in 1.5 ml) and the NADH consumption was determined at 340 nm over a period of time of 2 min.

Results:

Necrotic processes are associated with an increased release of lactate dehydrogenase [LDH]. As can be seen from Table 1, after exposure of the cells in a hypoxic atmosphere and subsequent reoxygenation an increase in the LDH release by more than 50% takes place. As a result of pretreatment with flupirtine, the necrosis induced by hypoxia and subsequent reoxygenation is prevented as can be seen from the lack of increase in LDH release compared with the control ($p<0.05$).

TABLE 1

Increase in LDH release
Control value: 21,13 ± 3.14 mU/ml/mg of protein

| Treatment | Increase in LDH release in comparison with the control (mU/ml/mg of protein) |
| --- | --- |
| Hypoxia 5 h + Reoxygenation 3 h | 13.52 ± 2.85 |
| Hypoxia 5 h + Reoxygenation 3 h + Flupirtine 100 µM | 1.19 ± 1.03 * |

One-sided ANOVA test, followed by the Dunnet test
* $p < 0.05$

These results show clearly that flupirtine is a promising medicament, in particular for the treatment of body disorders with cell-destroying processes, such as, for example, myocardial infarct, shock kidney, shock lung, senile macular degeneration or traumas as a result of mechanical, thermal, radiation or toxic influences suitable [sic].

In several in vitro and in vivo models, it was possible to demonstrate for flupirtine an NMDA-antagonistic and, associated with it, neuroprotective action. On the basis of these data, clinical use of flupirtine is conceivable, inter alia, in AIDS encephalopathy. For the origin of AIDS encephalopathy, it is discussed that infected macrophages release, inter alia, neurotoxins having an NMDA-antagonistic action, which then lead to nerve cell death via stimulation of the NMDA receptor (Lipton 1992).

In cell culture experiments, it was possible to demonstrate that both the NMDA- and also the HIV (gp120)-mediated neurotoxic action can be inhibited by flupirtine (Perovic et al. 1994).

It was a complete surprise that flupirtine is able to increase the expression of the apoptosis-inhibiting protein Bcl-2, whose occurrence is not only restricted to nerve cells. Bcl-2 is localized in the nuclear membrane, parts of the endoplasmic reticulum and the mitochondrial membrane.

Moreover, it was also surprisingly found that flupirtine is also able to inhibit necrotic cell death in vitro, as the reduced release of the cytoplasmic enzyme lactate dehydrogenase confirms. Increases in the lactate dehydrogenase occur in man, as is known, as a result of cell-destroying processes, inter alia, after myocardial infarct, in acute hepatitis or toxic liver damage.

Flupirtine can be administered for prophylaxis and therapy in a known manner in the following presentation forms:

Tablets, film-coated tablets, hard gelatin capsules, soft gelatin capsules, pellets, granules, sugar-coated tablets, suppositories, microcapsules, aqueous or oily suspensions, oily solutions, injection solutions for intramuscular administration and injection solutions for intravenous administration.

Suitable salts for the production of the medicament are all physiologically tolerable salts of flupirtine. For example, the hydrochloride, maleate, sulphate and gluconate of flupirtine are suitable.

The contents of flupirtine in the medicaments according to the invention are 0.1 mg–3000 mg, preferably 10 mg–500 mg. The individual doses of the medicament mentioned can be administered 1–5 times, preferably 1–times, daily.

The dosage details always relate to flupirtine as a base. If salts of flupirtine are employed, the molecular weight is to be recalculated accordingly.

The pharmaceutical handling of the compounds according to the invention takes place according to the customary standard methods. For example, flupirtine and the excipients and/or auxiliaries are well mixed by stirring or homogenizing, in general working at temperatures between 20 and 80° C., preferably 20 to 50° C.

What is claimed is:

1. A method of preventing or treating a disorder selected from the group consisting of myocardial infarct, shock kidney, shock lung, and senile macular degeneration comprising administering to a host in need thereof an effective amount of flupirtine or a pharmaceutically utilizable salt thereof.

2. The method of claim 1 wherein said disorder is senile macular degeneration.

3. The method of claim 1 wherein said disorder is myocardial infarct.

4. The method of claim 3 wherein flupirtine is administered in an amount between 0.1 mg and 3000 mg per day.

5. The method of claim 4 wherein flupirtine is administered in an amount between 10 mg and 1500 mg per day.

6. The method of claim 5 wherein flupirtine is administered in an amount between 10 mg and 500 mg per day.

* * * * *